United States Patent [19]

Vickers

[11] Patent Number: 4,911,154

[45] Date of Patent: Mar. 27, 1990

[54] SURGICAL PIN DRIVER

[76] Inventor: David W. Vickers, 225 Wickham Tce., Brisbane 4000, Australia

[21] Appl. No.: 69,138

[22] Filed: Jul. 2, 1987

[30] Foreign Application Priority Data

Jul. 4, 1986 [AU] Australia .............................. PH6737

[51] Int. Cl.⁴ .............................................. A61F 5/04
[52] U.S. Cl. ...................................... 606/104; 606/80
[58] Field of Search ....................... 128/70, 75, 83, 85, 128/84, 87, 87 B, 91 A, 92 B, 92 R, 92 EA, 92 V, 92 VD, 92 VK, 92 VL, 92 YF, 92 VS, 92 YD, 92 YC, 92 VY, 92 XV, 303 R; 81/64; 269/157, 229, 236

[56] References Cited

U.S. PATENT DOCUMENTS

| 157,293 | 12/1874 | *Pitt | 269/157 |
|---|---|---|---|
| 334,611 | 1/1886 | Reed | 269/157 |
| 461,322 | 10/1891 | Cunningham | 269/157 |
| 526,420 | 9/1894 | Thomas | 269/236 |
| 533,792 | 2/1895 | Donovan | 269/236 |
| 685,050 | 10/1901 | Kettlelson | 81/321 |
| 855,905 | 6/1907 | Rhoads | 269/236 |
| 914,182 | 3/1909 | Pfeffer | 128/92 VZ |
| 930,235 | 8/1909 | Sanders | 269/157 |
| 1,025,362 | 5/1912 | Beuoy | 128/321 |
| 4,442,837 | 4/1984 | Keatley | 128/321 |

Primary Examiner—Robert A. Hafer
Assistant Examiner—Charles H. Sam
Attorney, Agent, or Firm—Sughrue, Mion, Zinn, Macpeak & Seas

[57] ABSTRACT

A surgical pin driver having a pair of elongated clamping jaws terminating in a clamping handle is provided with a bearing member pivotally movable relative to the clamping jaws for engagement therewith to move the clamping jaws from an open position to a closed position and vice versa. A bridging member surrounds the clamping jaws and is pivotally attached to the bearing member. An actuating lever having an actuating handle is bifurcated at the end remote from the actuating handle so as to provide a gap which encloses the clamping jaws. The bearing member is formed as an extension of the actuating lever so that the clamping handle and the actuating handle are capable of being gripped in one hand for driving a pin clamped between the clamping jaws into bone.

14 Claims, 4 Drawing Sheets

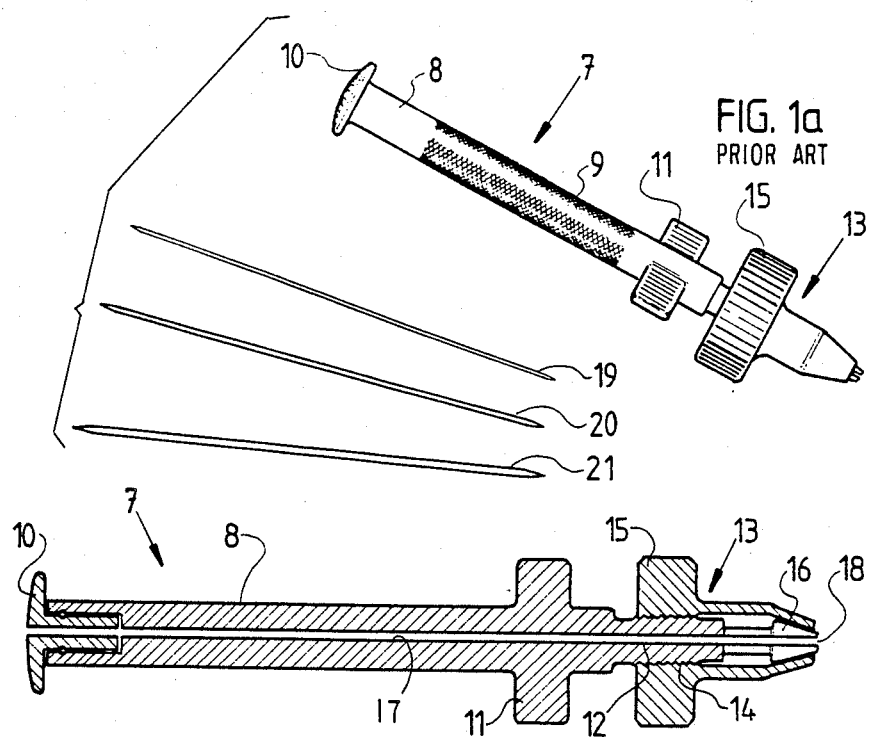
FIG. 1a PRIOR ART
FIG. 1b PRIOR ART
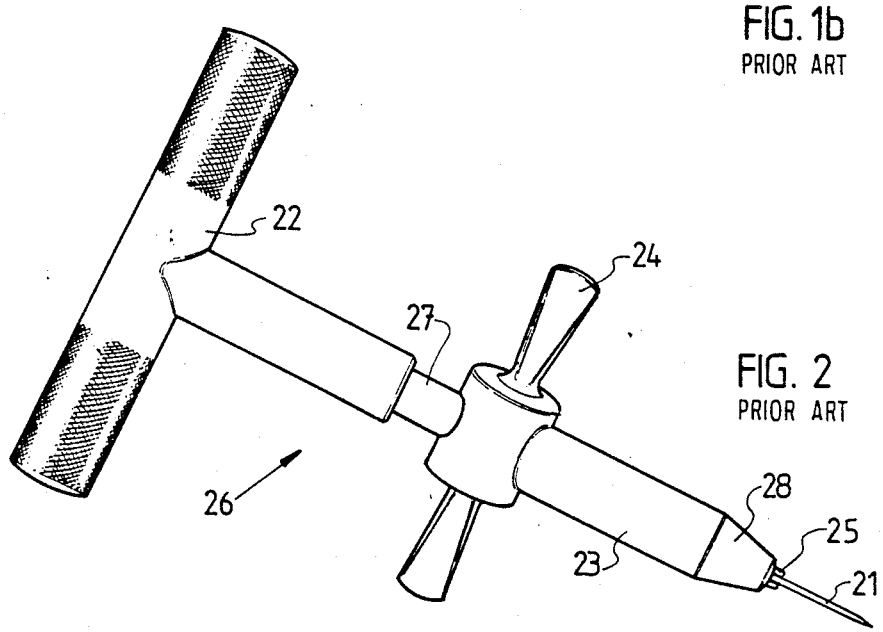
FIG. 2 PRIOR ART

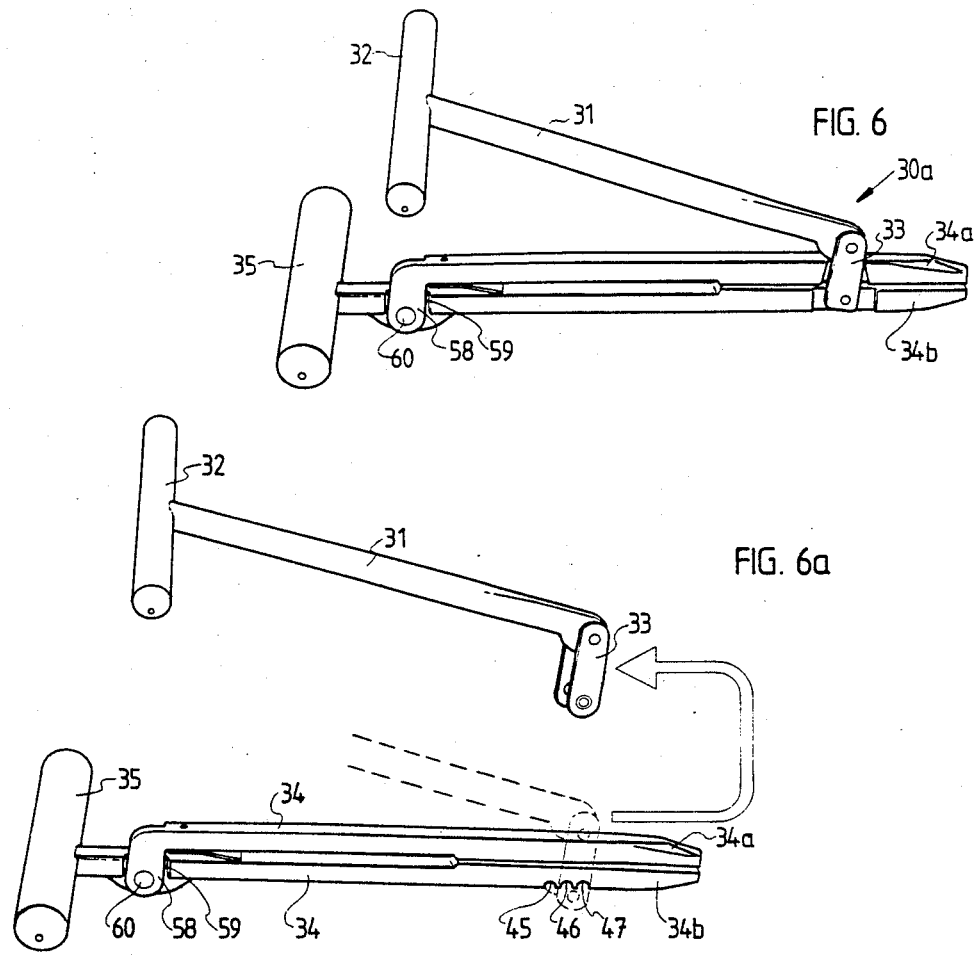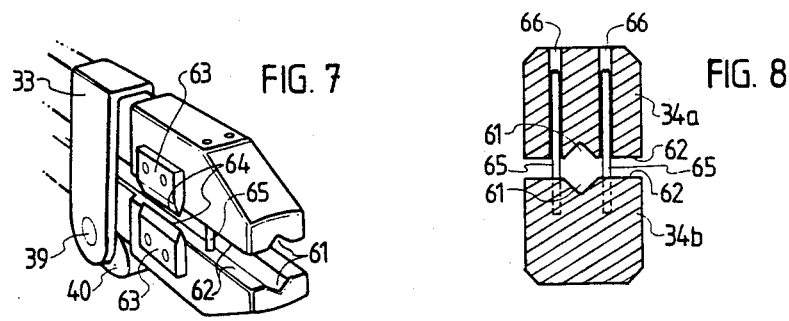

SURGICAL PIN DRIVER

BACKGROUND OF INVENTION

This invention relates to an improved surgical pin driver for the insertion of metal pins into bone.

Conventional surgical pin drivers have included a manually operated apparatus having a plurality of clamping members which were operated by a handle screw threadedly mounted to a mounting head of chuck for mounting the clamping members. Generally the handle was movable relative to the stationary mounting head and movement of the handle away from the mounting head caused the clamping jaws to open and movement of the handle toward the mounting head caused the clamping members to close. The clamping members were used to clamp a length of surgical pin or wire which was used for insertion into bone for knitting or pinning of fractures.

Manually operated surgical pin drivers of the type discussed above were subject to disadvantages in use. For example when driving a pin into bone it was initially necessary to open the clamping members for location of the pin or wire therein, close the clamping members and then manually drive the pin into the bone. This was achieved by a reciprocating pivotal movement of the forearm. However, in regard to driving the pin into bone it was necessary to place one hand on the bone so as to close the fracture as tightly as possible and the other hand was used to hold the surgical pin driver and operate as described above in regard to the aforesaid reciprocatable pivotal movement.

Therefore in regard to operation of the conventional surgical pin driver as described above it was necessary to use two hands in regard to unlocking or locking of the clamping members in relation to clamping of the pin or wire in the pin. A two handed operation was therefore essential in relation to adjustment of the pin when already driven into the bone and this was undesirable especially in regard to the fact that it was necessary to release one hand from gripping the bone. This had the unfortunate occurrence of causing separation of the bones along the fracture and thereby causing an unwanted gap between bone fragments. It also increased the danger of further fracturing occurring.

The above problems were exacerbated when it was borne in mind that it was necessary to release and regrip the surgical pin driver a number of times during the pinning operation.

Another disadvantage of the conventional manually operated surgical pin driver as described above was that often it was uncertain whether or not slippage of the pin in the bone had occurred. Slippage in fact had a tendency to occur especially if the pin was also driven through fatty tissue which may be present in certain circumstances. The only method of detection of slippage was to unload the pin from the chuck by using two hands with the undesirable consequences as described above and compare the exposed length of the pin with another identical pin to assess the length.

Also in the prior art manually operated surgical pin drivers efficient function depended upon proper lubrication of the moving parts. This could only be achieved by water in regard to a surgical instrument and thus the moving parts had a tendency to bind as well as to corrode or rust.

It was also to be appreciated not only were manually operated pin drivers known but also pin drivers were used which functioned in a similar manner to power drills. These power-actuated surgical pin drivers could be operated by one hand and thus the aforesaid disadvantages of manual pin drivers could be substantially alleviated. However, power driven surgical pin drivers were operated by use of compressed air and thus the associated equipment which included gas cylinders mounted on wheels and air hoses was extremely bulky and cumbersome and also extremely expensive. Also all the components required autoclaving between operations.

SUMMARY OF THE INVENTION

It therefore is an object of the present invention to provide a surgical pin driver which may alleviate the abovementioned disadvantages associated with the prior art.

The surgical pin driver of the invention includes:
- a pair of opposed elongate clamping jaws;
- a bearing member pivotally movable relative to the jaws for engagement therewith to move the jaws from an open position to a closed position and vice versa; and
- manually operable actuating means for actuating movement of said bearing member.

The pair of opposed elongate clamping jaws may be of any suitable type but preferably comprise two elongate members formed by rods or tubes of any suitable cross sectional shape which are provided with opposed clamping faces which are preferably planar.

In regard to location of a wire or pin in each clamping jaw there may be provided one locating groove in one clamping face or more preferably a pair of locating grooves in each opposed clamping face thereof.

There also may be provided guide means for the wire or pin each each clamping jaw and this may be of any suitable type. In one form there may be provided a row of guide lugs or projections bounding each side of a respective locating groove. Each guide lug may be retained in an associated guide socket so that on one planar clamping face there is provided a pair of rows of guide lugs bounding a first locating groove and on the other planar clamping face there is provided a mating pair of rows of sockets bounding a second locating groove.

The pair of clamping jaws are substantially parallel so that their grip on a maximum length of pins of varying diameters is ensured. The bearing member is suitably located adjacent the tips or free ends of each clamping jaw and the association of the clamping jaws with the bearing member is suitably achieved by a bridge or joint member described hereinafter.

At a fixed end of the clamping jaws or end remote from the tips or free ends each elongate member forming a respective clamping jaw is attached to each other in a suitable manner so as to provide each clamping jaw with an outwardly directed bias at their respective free ends. This may be achieved in a number of ways. In one example a spring may be located between the planar faces of each jaw at or adjacent their fixed ends. In another example the two elongate members forming the clamping jaws are formed from a single U shaped member and there is provided a weakened zone, thinned zone or tapered zone adjacent the common end or base of the U which provides the desired outwardly directed bias at the free ends.

The actuating means for actuating movement of the bearing member is preferably another elongate member again formed of rigid rod or tube and having any suitable cross sectional shape. The actuating member may also function as a handle member and to this end there may be provided a handle at an outer or free end thereof of the actuating member. The bearing member is suitably formed as an end portion of the actuating member and may either comprise a cam projection or curved or inwardly tapered end portion which is in bearing engagement with the clamping jaws on movement of the actuating member.

In the above embodiment the actuating member is suitably an actuating lever which is pivotally attached to a joint or bridge member which is suitably U shaped so that it encloses or surrounds the clamping jaws adjacent the free ends thereof. Preferably the bridge member is attached to an inner end portion of the actuating lever and this is accomplished in any suitable manner. In one arrangement a rivet or other suitable fastening member may extend between opposed arms of the U shaped bridge member below the clamping jaws and also through the inner end of the actuating lever. The rivet or fastening member in this embodiment may function as a pivot pin.

In another embodiment there may be provided cutting means for cutting the pin or wire when required and this may include a pair of opposed cutting jaws or cutting members which are each located on a respective clamping jaw. In this embodiment each cutting member may move to an operative cutting position when the clamping jaws are in the closed position.

In another arrangement the actuating lever may be releasably attached to the clamping jaws by the bridge member wherein the bridge member is releasably looped around the clamping jaws for disengagement when required. However, in a more preferred situation the actuating lever is permanently attached to the clamping jaws by the bridge member.

BRIEF DESCRIPTION OF THE DRAWINGS

Reference may now be made to a preferred embodiment as shown in the attached drawings wherein:

FIG. 1a is a view of one type of conventional surgical pin driver as well as three different types of pins of varying thicknesses for use in conjunction with the surgical pin driver;

FIG. 1b is a sectional view of the conventional surgical pin driver shown in FIG. 1a;

FIG. 2 is a view of an alternative type of conventional surgical pin driver;

FIG. 6 is a perspective view of an alternative type of surgical pin driver constructed in accordance with the invention which is different to that shown in FIG. 3;

FIG. 6a is an exploded view of the assembly in FIG. 6.

FIG. 7 is a detailed perspective view of the free ends or tips of the clamping jaws showing the cutting jaws;

FIG. 8 is a transverse sectional view through the cutting jaws of FIG. 7 showing the guide lugs and sockets as well as the locating grooves for the pin;

DETAILED DESCRIPTION OF THE INVENTION

Figure 3:
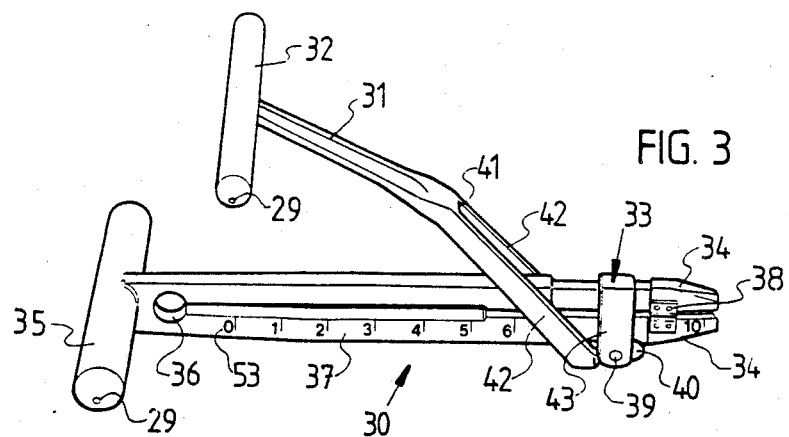
FIG. 3 is a perspective view of a surgical pin driver constructed in accordance with the invention.

In FIGS. 1a and 1b the conventional surgical pin driver 7 includes a handle 8, knurled or milled grip 9, end part 10, holding lugs 11, end portion 12 screw threadedly retained in mounting head or chuck 13 at 14, boss 15 of mounting head 13, clamping members 16 in bore 17 of mounting head 13, and end aperture 18 from which pins 19, 20 and 21 are all of varying diameters as shown. Upon rotation of mounting head 13 relative to handle 8 whereby mounting head 13 moved outwardly or away from handle 8 clamping members 16 moved away from engaging with pins 19, 20 or 21 and thus pins 19, 20 or 21 could be released from clamping members 16. Upon movement of mounting head 13 in the opposite direction clamping members 13 engaged or firmly gripped pins 19, 20 or 21. However, it will be appreciated that it required two hands to unlock clamping members 16 from engagement with the pin. One hand rotated boss 15 while the other hand grasped handle 8 at lugs 11.

The other conventional surgical pin driver shown in FIG. 2 was constructed on a similar principle. One hand grasped T handle 22 while the other hand rotated shank 23 by grasping holding lugs 24. Again as described in FIGS. 1a and 1b clamping members 25 of chuck 28 could then be released from or engaged with pin 21 as may be required. Again two hands were necessary for effective operation of surgical pin driver 26 shown in FIG. 2. Shank 23 had part 27 screw threadedly retained in a bore (not shown) of T handle 22.

Figure 4:
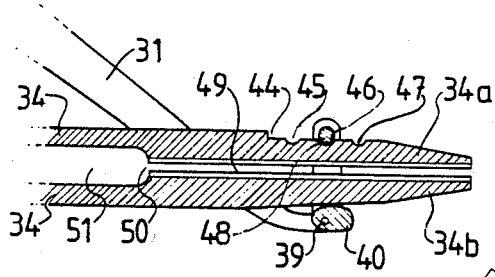
FIG. 4 is a sectional view through the clamping jaws of the surgical pin driver shown in FIG. 3 wherein the clamping jaws are in the open or partly open position.

The surgical pin driver 30 of the invention shown in FIG. 3 includes actuating lever 31, handle 32, U shaped bridge member 33, elongate clamping jaws 34, handle 35, weakened zone 36, scale 37, cutting jaws 38 and pivot pin 39 interconnecting actuating lever 31 to bridge member 33. Also shown is cam projection 40. Lever 31 may be bifurcated at 41 to form two branches 42 which extend on opposite sides of clamping jaws 34 as shown and thus be attached to opposed arms 43 of bridge member 33 by pivot pin 39. Apertures 29 may be formed in handles 32 and 35 for bending the ends of pin 19 after insertion into the bone. The apertures 29 may be of varying sizes corresponding to the sizes of pins 19, 20 or 21. Bridge member 33 may be attached to opposed jaws 34 in a number of suitable ways. As shown in FIG. 4 the upper clamping jaw 34a may be noticed at 44. Notch 44 may also include a plurality of retaining grooves 45, 46 and 47 which may all correspond to the correct position for retention of pins 19, 20 or 21 respectively. For example, when it is desired to use pin 19 groove 45 may be selected. Bridge member 33 includes a transverse pin 48 which is located in a selected groove 45, 46 or 47.

Figure 4A:
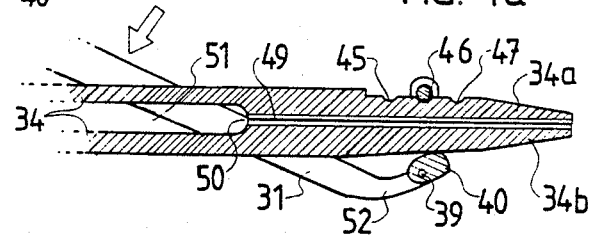
FIG. 4a is a similar view to FIG. 4 showing the clamping jaws in the closed position.

In FIG. 4 the upper jaw 34a and lower jaw 34b are shown in an open position. However, upon downward movement of actuating lever 31, as shown by the arrow, cam projection 40 may bear against the underside of clamping jaw 34b as shown to force jaws 34a and 34b into close proximity for effective retention of pin 19, 20 or 21. Thus gap 49 is considerably narrower in FIG. 4a then in FIG. 4. In fact in FIG. 4a gap 49 may disappear altogether and jaws 34a and 34b may terminate at 50 and elongate members 34 may continue rearwardly as shown to merge at handle 35. In practice members 34 may be substantially parallel and may be outwardly biassed to facilitate gripping of the pin when urged into the closed position by clamping protection 40. This is enhanced by weakened zone 36 shown in space 51 between elongate members 34. Cam projection 40 is suitably formed as an inner end protrusion of lever 31 which also may taper upwardly as shown at 52. Scale 37 may also have an origin O adjacent handle 35 as shown at 53. This means that the length of pin being utilised in an operation can be easily determined by the surgeon.

Figure 5:
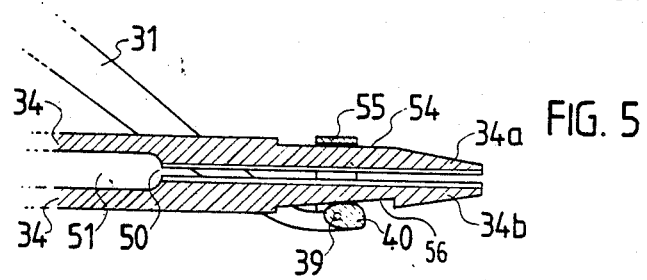
FIG. 5 is a sectional view through the clamping jaws of a surgical pin driver constructed in accordance with the invention showing a different means of attachment of the bridge member to the clamping jaws to that shown in FIG. 4.

In FIG. 5 notch 54 may be provided with a planar surface 54 which may engage with a top member 55 of bridge member 33. There also may be provided tapered recess 56 for engagement of cam projection 40. Tapered recess 56 may be used in substitution of notches 45, 46 and 47, which are all of varying diameter, so to provide a multiplicity of varying adjustment positions for use of pins of varying diameters 19, 20 or 21.

Figure 5A:
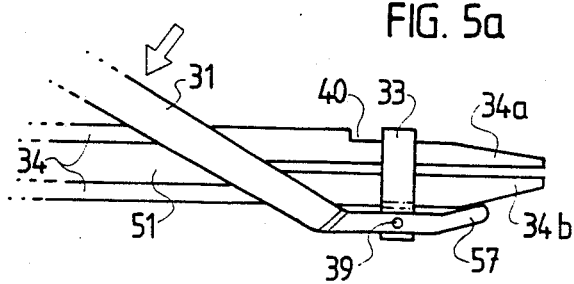
FIG. 5a is a view showing an alternative type of bearing member for use other than the cam projection shown in FIGS. 4, 4a and 5.

In FIG. 5a instead of cam projection 40 actuating lever may be provided with an upwardly extending bearing projection 52 as shown which upon downward movement of lever 31 may effectively close jaws 34a and 34b.

In FIG. 6 the surgical pin driver 30a is similar to the pin driver 30 already discussed above in regard to FIG. 3 with the exception that top elongate member 34 is formed with a downwardly extending part 58 which engages in recess 59 of bottom elongate member 34 and is retained therein by rivet 60. Also the assembly formed by actuating lever 31, bridge member 33, and cam projection 40 may be releasable from clamping jaws 34 if required. This is shown in FIG. 6a. However, a permanent attachment is preferred and this is utilised in the FIG. 3 embodiment.

In FIG. 7 there is also shown pin retaining grooves 61 which may be located in opposed planar undersurfaces 62 of jaws 34a and 34b. There also may be provided cutting jaws 63 having cutting edges 64 for severing of pins when required.

In FIG. 8 there may be provided a double row of guide pins 65 wherein each row may be bound a respective pin locating groove 61 as shown. This is indicated on the bottom surface 62. On the top surface 62 there may also be provided a double row of meting sockets 66 wherein each row of sockets may also bound a respective pin locating groove 62.

Figure 9A:
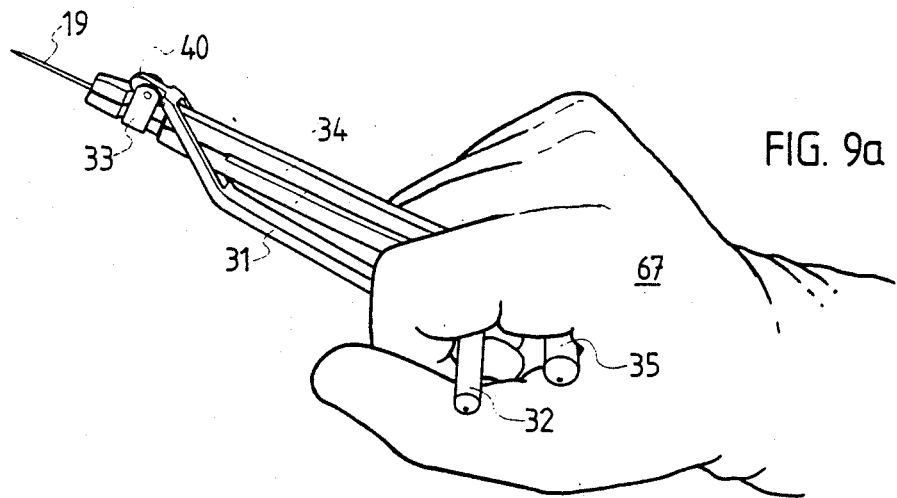
FIG. 9a is a perspective view showing how the surgical pin driver of the invention is grasped by the hand in one type of grip that may be used.

In FIG. 9a one type of hand grip is shown for insertion of pin 19 into bone by use of hand 67 securely gripping handles 32 and 35.

Figure 9B:
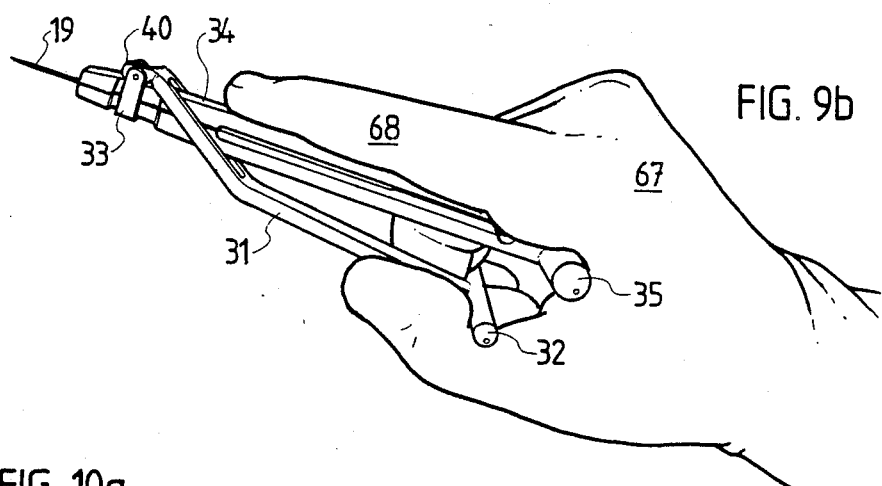
FIG. 9b is a perspective view similar to FIG. 9a showing an alternative hand grip that may be used.

In FIG. 9b an alternative type of hand grip is shown for driving pin 19 into bone. The finger 68 may be used to guide and pilot the pin 19 in the desired orientation and alignment. A reciprocating pivotal movement of the hand is utilised.

Figure 10A:
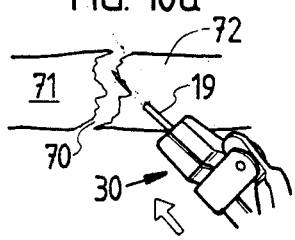
FIGS. 10a, 10b, 10c show the various stages which are applicable in pinning a fracture in bone.
Figure 10B:
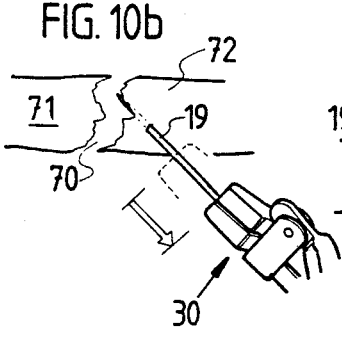
Figure 10C:
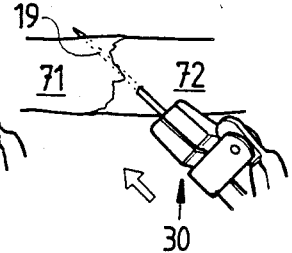

In FIGS. 10a, 10b and 10c the sequence of events in pinning a fracture 70 in bases 71, 72 is shown. FIG. 10a shows initial insertion using the grip shown in FIG. 9a or FIG. 9b. Thereafter the surgical pin driver 30 may be released and withdrawn leaving pin 19 inserted into the bone 72 short of fracture 70. This is shown in FIG. 10b the arrow. In FIG. 10c the pin 19 may then be driven into bone 71 so as to complete efficient pinning of the fracture 70. The pin may be released and regripped a number of times.

It will therefore be appeciated that relative movement of pin driver 30 to pin 19 is possible and that the pin may be left inserted in the bone. Unlocking of clamping jaws 34 is efficiently carried out by one hand 67 leaving the other hand securely gripping bones 71, 72 to keep the gap in fracture 70 as minimal as possible.

The pin 19 may be easily withdrawn or pushed further into the bone when required and the use of scale 37 shows that slippage may be effectively detected by indicating what length of pin has been inserted.

I claim:

1. A surgical pin driver comprising a pair of elongate clamping jaws terminating in a clamping handle;
   a bearing member pivotally movable relative to said clamping jaws for engagement therewith to move said clamping jaws from an open position to a closed position and vice versa;
   a bridging member surrounding said clamping jaws wherein said bearing member is pivotally attached thereto;
   an actuating lever having an actuating handle which is bifurcated at an end remote from said actuating handle so as to provide a gap which encloses said clamping jaws whereafter said bearing member is formed as an extension of said actuating lever whereby in use both said clamping handle and said actuating handle are capable of being gripped in one hand for driving a pin into a bone wherein said pin is clamped between said pair of clamping jaws.

2. A surgical pin driver as claimed in claim 1 wherein there is provided a pair of pin locating grooves each located on opposed clamping faces of said jaws.

3. A surgical pin driver as claimed in claim 2 wherein there is provided a pair of guide lugs wherein each guide lug bounds a respective side of a first pin locating groove.

4. A surgical pin driver as claimed in claim 3 wherein there is provided a pair of mating sockets for said pair of guide lugs wherein each of said sockets bounds a respective side of a second pin locating groove.

5. A surgical pin driver as claimed in claim 1 wherein there is further provided biassing means associated with the jaws so as to facilitate movement of each jaw away from each other or the closed portion.

6. A surgical pin driver as claimed in claim 5 wherein each clamping jaw is joined to each other at a common end in such a manner so as to produce said biassing means.

7. A surgical pin driver as claimed in claim 6 wherein there is produced a weakened zone adjacent said common end.

8. A surgical pin driver as claimed in claim 1 wherein there is provided a pair of cutting jaws each located on a respective clamping jaw.

9. A surgical pin driver as claimed in claim 1 wherein the bridging member is substantially U shaped and said bearing member is interposed between opposed arms of the U and a pivot pin interconnects said bearing member and each opposed arm.

10. A surgical pin driver as claimed in claim 9 wherein said bridge member is adjustably movable relative to the pair of clamping jaws so as to vary the gap between said jaws relative to pins of varying diameter.

11. A surgical pin driver as claimed in claim 10 wherein one clamping jaw is provided with a plurality of retaining grooves for retention of said bearing member.

12. A surgical pin driver as claimed in claim 1 wherein the bearing member is a cam projection.

13. A surgical pin driver as claimed in claim 1, wherein said elongate clamping jaws include an upper clamping jaw and a lower clamping jaw and said bearing member is located below and in abutting relationship with said lower clamping jaw.

14. A surgical pin as claimed in claim 1, wherein said clamping handle extends transversely relative to said elongate clamping jaws and said actuating handle extends transversely relative to said lever and parallel to said clamping handle.

* * * * *